(12) United States Patent
Kurumatani et al.

(10) Patent No.: US 9,457,032 B2
(45) Date of Patent: Oct. 4, 2016

(54) THERAPEUTIC AGENT FOR RENAL FAILURE

(75) Inventors: Hajimu Kurumatani, Kamakura (JP); Motohiro Suzuki, Kamakura (JP)

(73) Assignee: Toray Industries, Inc. (JP)

( * ) Notice: Subject to any disclaimer, the term of this patent is extended or adjusted under 35 U.S.C. 154(b) by 672 days.

(21) Appl. No.: 12/368,356

(22) Filed: Feb. 10, 2009

(65) Prior Publication Data
US 2009/0163584 A1 Jun. 25, 2009

Related U.S. Application Data

(63) Continuation of application No. 11/319,821, filed on Dec. 28, 2005, now abandoned, which is a continuation of application No. 10/289,626, filed on Nov. 7, 2002, now abandoned, which is a continuation of application No. 09/743,275, filed as application No. PCT/JP00/02973 on May 10, 2000, now abandoned.

(51) Int. Cl.
*A61K 31/343* (2006.01)
*A61K 31/558* (2006.01)

(52) U.S. Cl.
CPC ........... *A61K 31/558* (2013.01); *A61K 31/343* (2013.01)

(58) Field of Classification Search
None
See application file for complete search history.

(56) References Cited

U.S. PATENT DOCUMENTS

| | | | |
|---|---|---|---|
| 4,474,802 A | 10/1984 | Ohno et al. | |
| 4,822,804 A | 4/1989 | Ohno et al. | |
| 5,244,910 A | 9/1993 | Baker et al. | |
| 5,276,031 A | 1/1994 | Kleinert | |
| 6,656,502 B1 * | 12/2003 | Hara et al. | 424/464 |

FOREIGN PATENT DOCUMENTS

| | | |
|---|---|---|
| CA | 2303343 | 3/1999 |
| EP | 1 016 408 A1 | 7/2000 |
| JP | 2-12226 B2 | 3/1990 |
| JP | 03-163023 | 7/1991 |
| JP | 11-189536 | 7/1999 |
| WO | 96/16661 | 6/1996 |
| WO | WO 99/13880 A1 | 3/1999 |

OTHER PUBLICATIONS http://www.kidney.org/kidneydisease/howkidneyswrk.cfm, 2011.*
Stier et al., Beneficial Action of Beraprost Sodium, a Prostacyclin Analog, in Stroke-Prone Rats, 1997, Journal of Cardiovascular Pharmacology, vol. 30, pp. 285-293.*
Grandaliano et al., Monocyte Chemotactic Peptide-1 Expression in Acute and Chronic Human Nephritides: A Pathogenetic Role in Interstitial Monocyte Recruitment, 1996, J. Am. Soc. Nephrol., vol. 7, pp. 906-913.*
Umeda et al., Prostaglandins and Diabetic Nephropathy, 1995, Journal of Diabetes and Its Complications, vol. 9, pp. 334-336.*
Lascano et al. "Kidney Function Assessment by Creatinine-Based Estimation Equations", Cleveland Clinic, 2010, http://www.clevelandclinicmeded.com/medicalpubs/diseasemanagement/nephrology/kidney-function/, accessed Oct. 3, 2014,8 pages.*
Medscape: "Chronic Kidney Disease" http://emedicine.medscape.com/article/238798-overview, accessed Oct. 5, 2014, 4 pages.*
S. Moncada et al., An enzyme isolated from arteries transforms prostaglandin endoperoxides to an unstable substance that inhibits platelet aggregation, *Nature*, vol. 263, Oct. 21, 1976, pp. 663-665.
M. Tobimatsu et al., Effects of a stable prostacyclin analog on experimental ischemic acute renal failure, *Annals of Surgery*, 209/1, 1988, pp. 65-70. Abstract.
Eduardo Villa et al., Cicaprost, a Prostacyclin Analog, Protects Renal Function in Uninephrectomized Dogs in the Absence of Changes in Blood Pressure, *American Journal of Hypertension*, vol. 6, No. 4, Apr. 1993, pp. 253-257.
Yuji Tajiri, RINSHOTOKENKYU, *Clinic and Research*, vol. 71, No. 6, Jun. 1994, pp. 72-76.
E. Franek et al., Angiotensin-Converting Enzyme Inhibitors and Nephroprotection, *Expert Opinion on Investigational Drugs*, 4(11), 1995, pp. 1139-1149, Abstract.
Fumio Umeda et al., Prostaglandins and Diabetic Nephropathy, *Journal of Diabetes and Its Complications*, 9, 1995, pp. 334-336.
Y. Utsunomiya et al., Attenuation of immune complex nephritis in NZB/W $F_1$ mice by a prostacyclin analogue, *Clin. Exp. Immunol.*, 99(3), 1995, pp. 454-460.
P. Boucck, Care of Patients with Diabetic Nephropathy, *Casopis Lekaru Ceskych*, 136(22), 1997, pp. 689-692, Abstract.
Charles T. Stier, Jr., et al., Beneficial Action of Beraprost Sodium, a Prostacyclin Analog, in Stroke-Prone Rats, *Journal of Cardiovascular Pharmacology*, 30(3), 1997, pp. 285-293.
T. Inukai et al., Clinical evaluation of the administration of beraprost sodium on diabetic nephropathy in patients with non-insulin-dependent diabetes mellitus, *Japanese Pharmacology and Therapeutics*, 26/11, 1988, pp. 117-122, Abstract.
Masahiko Kushiro et al., Therapeutic effects of prostacyclin analog on crescentic glomerulonephritis of rat, *Kidney International*, vol. 53, No. 3, 1998, pp. 1314-1320.
A.G. Jardine et al., ACE Inhibition in Chronic Renal Failure and in the Treatment of Diabetic Nephropathy : Focus on Spirapril, *Journal of Cardiovascular Pharmacology*, 34(Suppl. 1), 1999, pp. S31-S34, Abstract.
Masateru Yamada et al., Amelioration by beraprost sodium, a prostacyclin analogue, of established renal dysfunction in rat glomerulonephritis model, *European Journal of Pharmacology*, 449(1-2), Aug. 2, 2002, pp. 167-176, Abstract.
El Nahas, A.M. et al., Renal Fibrosis: Insights into Pathogenesis and Treatment, *Int. J. Biochem. Cell. Biol.*, 1997, vol. 29, No. 1, pp. 55-62.
Szöcs, E. et al., "Functional Changes in Compensatory Hypertrophy of the Canine Kidney after Uninephrectomy," *Acta Physiologica Academiae Scientiarum Hungaricae, Tomus*, 1978, vol. 51, No. 1-2, pp. 23-40.
Robertson, J.L. et al., "Long-Term Renal Responses to High Dietary Protein in Dogs with 75% Nephrectomy," *Kidney International*, 1986, vol. 29, pp. 511-159.
Liu, C-T. et al., "Effect of Uninephrectomy on Kidney Weight and Renal Function in the Dog," *The Journal of Urology*, Sep. 1968, vol. 100, pp. 215-219.

(Continued)

*Primary Examiner* — Jeffrey S Lundgren
*Assistant Examiner* — Meghan Finn
(74) *Attorney, Agent, or Firm* — DLA Piper LLP (US)

(57) ABSTRACT

A therapeutic agent for renal failure including, as an active ingredient, a 4,8-inter-m-phenylene prostaglandin $I_2$ derivative, and also a method for treatment of renal failure using the same.

9 Claims, No Drawings

(56) References Cited

OTHER PUBLICATIONS

Hostetter, T.H. et al., Hyperfiltration in Remnant Nephrons: a Potentially Adverse Response to Renal Ablation, *The American Physiological Society,* 1981, pp. F85-F93.

*Harrison's Principles of Internal Medicine,* Eleventh Edition, Cover and Contents,1958, 4 pages.

Finco, D.R. et al., "Effects of Aging and Dietary Protein Intake on Uninephrectomized Geriatric Dogs," *Am J Vet Res,* Sep. 1994, vol. 55, No. 9, pp. 1282-1290.

Brenner, B.M., "Remission of Renal Disease: Recounting the Challenge, Acquiring the Goals," *The Journal of Clinical Investigation,* Dec. 2002, vol. 110, No. 12, pp. 1753-1758.

Bourgoignie, J.J. et al., "Glomerular Function and Morphology after Renal Mass Reduction in Dogs," *J Lab Clin Med,* Apr. 1987, vol. 109, pp. 380-388.

Zuckerman, A. et al., "Regional Renal Nitric Oxide Release in Stroke-Prone Spontaneously Hypertensive Rats," *Hypertension,* Dec. 1997, vol. 30, No. 6, pp. 1479-1486.

Nishio, S. et al., "The In Vitro and Ex Vivo Antiplatelet Effect of TRK-100, a Stable Prostacyclin Analog, in Several Species," *Japan. J. Pharmacol.,* 1988, vol. 47, pp. 1-10.

\* cited by examiner

THERAPEUTIC AGENT FOR RENAL FAILURE

TECHNICAL FIELD

The present invention relates to a therapeutic agent for renal failure comprising, as an active ingredient, a 4,8-inter-m-phenylene prostaglandin $I_2$ derivative or a pharmacologically acceptable salt thereof.

BACKGROUND ART

Prostaglandins (PGs) are a class of naturally occurring compounds with a wide variety of physiological activities, which have a common prostanoic acid skeleton. Naturally occurring PGs are classified into PGAs, PGBs, PGCs, PGDs, PGEs, PGFs, PGGs, PGHs, PGIs and PGJs according to the structural characteristics of the 5-membered ring in the skeleton. It is and also classified into subclasses 1, 2, 3 and so on according to the ansaturation and oxidation. Various synthetic analogues of these PGs are known. Among these, $PGI_2$, which is a typical PGI derivative, is called prostacycline (see Nature, vol. 268, p. 688, 1976). $PGI_2$ is known as a substance having potent platelet aggregation inhibiting activity and peripheral vasodilator activity. Japanese Examined Patent Application Publication Nos. 2-12226, 2-57548 and 1-53672 have described 4,8-inter-m-phenylene $PGI_2$ derivatives, in which the exo-enol ether moiety that is a structurally characteristic portion of $PGI_2$ is converted to an inter-m-phenylene moiety to substantially improve the instability of $PGI_2$. However, it has not yet recognized that such derivatives have therapeutic activities on renal failure.

Renal failure is a condition characterized by decreased number of functional nephrons, resulting in reduced excretion of nitrogenous metabolic products and eventually causing the failure to maintain homeostasis in the biological environment. Specifically, this can be said to be a condition in which blood urea nitrogen (BUN) and creatinine levels are continuously increased. Renal failure is categorized into two primary types: acute renal failure in which the onset is abrupt and recovery may occur; and chronic renal failure which is slowly progressive but irreversible.

Acute renal failure is primarily categorized into the following two types: oliguric acute renal failure which is frequently complicated by water, electrolyte and acid-base imbalances and manifested by oliguria or anuria; and non-oliguric acute renal failure in which decreased urinary volume is not found.

Acute renal failure is also categorized into the following three types according to its cause: 1) pronephric acute renal failure in which reduction of renal blood flow occurs due to systemic hemodynamic changes such as prerenal dehydration and shock, causing reduced glomerular filtration rate; 2) renal acute renal failure which is induced by glomerular and tubular disorders such as acute tubular necrosis; and 3) postrenal acute renal failure which is caused by obstruction of the urinary tract, e.g., by a calculus. According to the clinical manifestations, it can also be categorized into oliguric, uretic and recovery stages. In the treatment of acute renal failure, it is important to track down its cause and sufficiently perform systemic control of the patient. Such treatment includes two major forms, conservative treatment and dialytic treatment. According to the conservative treatment, in the oliguric stage, excessive water drinking is avoided and the amount of protein intake is restricted, while simultaneously supplying a sufficient amount of calories. In the oliguric stage, or when heart failure has occurred, then sodium intake is restricted. In contrast, in the uretic stage, potassium intake is increased. Generally in the oliguric stage, calcium intake is restricted. In the case where BUN is 60 mg/dl or higher or rises by 30 mg/dl or more per day or hyperkalemia or heart failure is found, then it is recommended to perform an early frequent dialysis.

Chronic renal failure is a condition in which gradual reduction in renal functions occurs due to a chronically progressive renal disease, in which the reduced renal functions are manifested as the insufficiency of all functions for which the normal kidney is responsible. The causal diseases of chronic renal failure are all of the nephropathic diseases, including primary renal diseases, nephropathy in systemic diseases, congenital renal diseases, renal infections, nephropathy induced by any nephrotoxic substance and obstructive urinary diseases. As seen in the clinical background of patients to whom dialysis has been introduced for treatment of chronic renal failure, the primary causal diseases of chronic renal failure may include chronic glomerulonephritis, diabetic nephropathy, chronic pyelonephritis, nephrosclerosis and cystic kidney. Among these, chronic glomerulonephritis and diabetic nephropathy make up a large proportion. The proportion of diabetic nephropathy as the causal disease in the total cases, however, remarkably increases as the number of diabetic patients rapidly increases in recent years.

As stated above, renal failure may be caused by various diseases. However, all types of renal failure have particular common clinical manifestations regardless of their causal diseases, such as lung congestion and congestive heart failure associated with reduced urinary volume; neurological or mental complaints associated with advanced uremia; anemia caused by reduced production of erythropoietin in the kidney; electrolyte imbalance, such as hyponatremia and hyperkalemia; gastrointestinal complaints; defect of bone metabolism; and defect of carbohydrate metabolism.

For the treatment of chronic renal failure in the conservative stage, dietary therapy including a low-protein, high-calorie diet is basically employed. In this case, it is required to restrict sodium chloride intake and water intake and to use an antihypertensive agent to control the hypertention which may be a risk factor for exacerbation of renal failure. However, such dietary therapy and the treatment with an antihypertensive agent as mentioned above produce unsatisfactory effects. Therefore, the number of patients who inevitably have hemodialysis goes on increasing year by year due to the manifestation of uremic symptoms caused by the advanced disorders of renal functions. In patients with renal failure who have entered into dialysis, remarkable improvement in the rate of prolongation of life has been achieved due to the improved hemodialysis therapy in recent years. However, there still remain problems in that the patients are unavoidable to visit the hospital twice or three times a week, that defects of erythrocyte production or maturation may occur, that complications will follow which may caused by the accumulation of aluminum and β2-microglobulin in a body occurring after the long-term dialysis, and so on.

The object of the present invention is to provide a therapeutic agent for renal failure on which already-existing drugs or agents show unsatisfactory effects.

DISCLOSURE OF INVENTION

The present invention provides a therapeutic agent for renal failure comprising, as an active ingredient, a 4,8-inter-m-phenylene prostaglandin $I_2$ derivative or a pharmacologically acceptable salt thereof.

BEST MODE FOR CARRYING OUT THE INVENTION

The 4,8-inter-m-phenylene prostaglandin $I_2$ derivative according to the present invention is represented by the following formula (I):

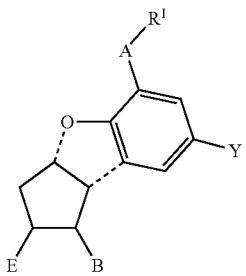

wherein:
$R^1$ represents:
(A) $COOR^2$
  wherein $R^2$ represents:
  1) hydrogen or a pharmacologically acceptable positive ion;
  2) a straight-chain $C_{1-12}$ alkyl group or a branched $C_{3-14}$ alkyl group;
  3) —Z—$R^3$
    wherein Z represents a valence bond or a straight-chain or branched alkylene group represented by $C_tH_{2t}$ where t represents an integer from 1 to 6; and $R^3$ represents a $C_{3-12}$ cycloalkyl group unsubstituted or substituted by 1 to 3 substituents of $R^4$ where $R^4$ is hydrogen or a $C_{1-5}$ alkyl group;
  4) —$(CH_2CH_2O)_nCH_3$
    wherein n represents an integer from 1 to 5;
  5) —Z—$Ar^1$
    wherein Z has the same meaning as defined above; and $Ar^1$ represents phenyl, α-naphthyl, β-naphthyl, 2-pyridyl, 3-pyridyl, 4-pyridyl, α-furyl, β-furyl, α-thienyl, β-thienyl or substituted phenyl (wherein the substituted phenyl contains at least one substituent of chlorine, bromine, fluorine, iodine, trifluoromethyl, a $C_{1-4}$ alkyl group, nitro, cyano, methoxy, phenyl, phenoxy, p-acetamidobenzamide, —CH=N—NH—C(=O)—$NH_2$, —NH—C(=O)-Ph, —NH—C(=O)—$CH_3$ or —NH—C(=O)—$NH_2$);
  6) —$C_tH_{2t}COOR^4$
    wherein each of $C_tH_{2t}$ and $R^4$ has the same meaning as defined above;
  7) —$C_tH_{2t}N(R^4)_2$
    wherein each of $C_tH_{2t}$ and $R_4$ has the same meaning as defined above;
  8) —$CH(R^5)$—C(=O)—$R^6$,
    wherein $R^5$ represents hydrogen or benzoyl; and $R^6$ represents phenyl, p-bromophenyl, p-chlorophenyl, p-biphenyl, p-nitrophenyl, p-benzamidophenyl or 2-naphthyl;
  9) —$C_pH_{2p}$—W—$R^7$
    wherein W represents —CH=CH—, —CH=$CR^7$— or —C≡C—; $R^7$ represents hydrogen or a straight-chain or branched $C_{1-30}$ alkyl or aralkyl group; and p represents an integer from 1 to 5; or
  10) —$CH(CH_2OR^8)_2$
    wherein $R^8$ represents a $C_{1-30}$ alkyl or acyl group;
(B) —$CH_2OH$;
(C) —C(=O)$N(R^9)_2$
  wherein $R^9$ represents hydrogen or a straight-chain $C_{1-12}$ alkyl group, a branched $C_{3-12}$ alkyl group, a $C_{3-12}$ cycloalkyl group, a $C_{4-13}$ cycloalkylalkylene group, a phenyl group, a substituted phenyl group (wherein the substitute or substituents are the same radicals as defined for (A)-5) described above), a $C_{7-12}$ aralkyl group, or —$SO_2R^{10}$ where $R^{10}$ represents a $C_{1-10}$ alkyl group, a $C_{3-12}$ cycloalkyl group, a phenyl group, a substituted phenyl group [wherein the substitute or substituents are the same radicals as defined for (A)-5] described above] or a $C_{7-12}$ aralkyl group; provided that the two $R^9$ radicals are the same as or different from each other, but when one represents —$SO_2R^{10}$, then the other does not represent —$SO_2R^{10}$; or
(D) —$CH_2OTHP$ (wherein THP represents a tetrahydropyranyl group);
A represents:
  1) —$(CH_2)_m$—;
  2) —CH=CH—$CH_2$—;
  3) —$CH_2$—CH=CH—;
  4) —$CH_2$—O—$CH_2$—;
  5) —CH=CH—;
  6) —O—$CH_2$—; or
  7) —C≡C—
    wherein m represents an integer from 1 to 3;
Y represents hydrogen, a $C_{1-4}$ alkyl group, chlorine, bromine, fluorine, formyl, methoxy or nitro group;
B represents —X—C($R^{11}$)($R^{12}$)$OR^{13}$
  wherein:
  $R^{11}$ represents hydrogen or a $C_{1-4}$ alkyl group;
  $R^{13}$ represents hydrogen, a $C_{1-14}$ acyl group, a $C_{6-15}$ aroyl group, tetrahydropyranyl, tetrahydrofuranyl, 1-ethoxyethyl or t-butyl;
  X represents:
    1) —$CH_2$—$CH_2$—;
    2) —CH=CH—; or
    3) —C≡C—; and
  $R^{12}$ represents:
    1) a straight-chain $C_{1-12}$ alkyl group or a branched $C_{3-14}$ alkyl group;
    2) —Z—$Ar^2$;
      wherein Z has the same meaning as defined above; and $Ar^2$ represents phenyl, α-naphthyl, β-naphthyl, or at least one chlorine, bromine, fluorine, iodine, trifluoromethyl, a $C_{1-4}$ alkyl group, nitro, cyano, methoxy, phenyl or phenoxy-substituted phenyl, or
    3) —$C_tH_{2t}OR^{14}$
      wherein $C_tH_{2t}$ has the same meaning as defined above; and $R^{14}$ represents a straight-chain $C_{1-6}$ alkyl group, a branched $C_{3-6}$ alkyl, phenyl, or at least one chlorine, bromine, fluorine, iodine, trifluoromethyl, an $C_{1-4}$ alkyl, nitro, cyano, methoxy, phenyl or phenoxy-substituted phenyl, cyclopentyl, cyclohexyl, or a cyclopentyl or cyclohexyl substituted by 1 to 4 straight-chain $C_{1-4}$ alkyl groups;

4) —Z—$R^3$ wherein each of Z and $R^3$ has the same meaning as defined above;

5) —$C_tH_{2t}$—CH=C($R^{15}$)$R^{16}$ wherein $C_tH_{2t}$ has the same meaning as defined above; and $R^{15}$ and $R^{16}$ independently represent hydrogen, methyl, ethyl, propyl or butyl group; or 6) —$C_uH_{2u}$—C≡C—$R^{17}$ wherein u represents an integer from 1 to 7; $C_uH_{2u}$ represents a straight-chain or branched alkylene group; and $R^{17}$ represents a straight-chain $C_{1-6}$ alkyl group; and E represents hydrogen or —$OR^{18}$ wherein $R^{18}$ represents a $C_{1-12}$ acyl group, a $C_{7-15}$ aroyl group or $R^2$ (wherein $R^2$ has the same meaning as defined above); and the formula is in the isomeric d-form, l-form or dl-form.

The therapeutic agent for renal failure according to the present invention comprises, as an active ingredient, a 4,8-inter-m-phenylene prostaglandin $I_2$ derivative represented by the formula (I) above or a pharmacologically acceptable salt thereof.

Among the 4,8-inter-m-phenylene prostaglandin $I_2$ derivatives described above, those derivatives described below and pharmacologically acceptable salt thereof are preferably used which are represented by the formula (I) above wherein:

$R^1$ represents $COOR^2$ wherein $R^2$ represents hydrogen or a pharmacologically acceptable positive ion;

A represents:

1) —$(CH_2)_m$—; or

2) —$CH_2$—CH=CH— wherein m represents an integer from 1 to 3;

Y represents hydrogen;

B represents —X—C($R^{11}$)($R^{12}$)$OR^{13}$ wherein each of $R^{11}$ and $R^{13}$ represent hydrogen;

X represents:

1) —CH=CH—; or

2) —C≡C—; and $R^{12}$ represents:

1) —Z—$Ar^2$;

2) —Z—$R^3$; or

3) —$C_uH_{2u}$—C≡C—$R^{17}$ wherein Z represents a valence bond or a straight-chain or branched alkylene group represented by $C_tH_{2t}$ where t represents an integer from 1 to 6; $Ar^2$ represents phenyl, α-naphthyl, β-naphthyl, or at least one chlorine, bromine, fluorine, iodine, trifluoromethyl, a $C_{1-4}$ alkyl group, nitro, cyano, methoxy, phenyl or phenoxy-substituted phenyl; $R^3$ represents a $C_{3-12}$ cycloalkyl group; u represents an integer from 1 to 7; $C_uH_{2u}$ represents a straight-chain or branched alkylene group; and $R^{17}$ represents a straight-chain $C_{1-6}$ alkyl group; and E represents —OH. A particularly preferable derivative is beraprost sodium having the following formula.

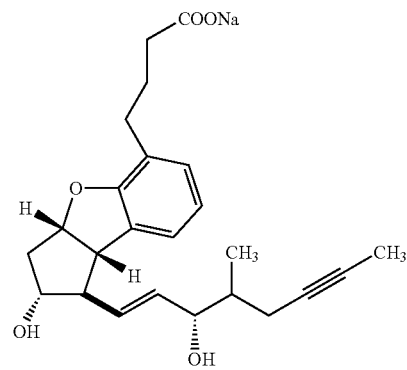

The 4,8-inter-m-phenylene prostaglandin $I_2$ derivative of the present invention can be produced by any known process. For example, a compound represented by the formula (I) above or a salt thereof may be produced according to the process described in Japanese Examined Patent Application Publication No. 1-53672.

In the present invention, the 4,8-inter-m-phenylene prostaglandin $I_2$ derivative can be administered at a dose of 0.001 to 1000 mg per adult subject once to three times a day.

The therapeutic agent for renal failure of the present invention may comprise the derivative alone or a combination of plural types of the derivatives and may be administered as is. Alternatively, the therapeutic agent may be administered orally in the form of a solid preparation containing an additive or additives shown below.

The causal disease of renal failure to be treated in the present invention may include all of the nephropathic diseases, such as primary renal diseases, nephropathies in systemic diseases, congenital renal diseases, renal infections, nephropathies induced by any nephrotoxic substance and obstructive urinary diseases. Specific examples of the causal disease include, but are not limited to, chronic glomerulonephritis, diabetic nephropathy, chronic pyelonephritis, acute progressive nephritis, gestosis, cystic kidney, nephrosclerosis, malignant hypertension, aephropathies accompanied by various collagen diseases such as SLE, amyloid kidney, gouty kidney, disbolic renal failure, tuberculosis, renal calculosis, malignant tumor in the kidney and urinary tracts, obstructive urinary tract diseases, myeloma and renal hypoplasia.

The renal failure to be treated with the therapeutic agent of the present invention is not particularly limited to either of acute or chronic type. However, the therapeutic agent is especially effective on chronic renal failure for which no effective therapy has currently been established and can delay the entrance into dialysis. Even when entered into dialysis, the therapeutic agent may be effective for the preservation of functions of the remained kidney.

The additive may include excipients, such as starches, lactose, sucrose, glucose, mannitol, calcium carbonate and calcium sulfate; binders, such as starches, dextrin, gum arabic, gum tragacanth, methyl cellulose, gelatin, polyvinyl pyrrolidone and polyvinyl alcohol; disintegrating agents, such as starches, polyvinyl pyrrolidone and crystalline cellulose; lubricants, such as magnesium stearate and talk; coloring agents; flavoring agents; and so on.

The 4,8-inter-m-phenylene prostaglandin $I_2$ derivative to be used in the present invention may be administered in various dosage forms. Specifically, the dosage form may be any conventional one, such as tablets, dragees, powders, granules, troches, capsules, pills, syrup and spray.

The derivative may also be administered parentally in the form of a sterile solution. Sodium chloride, glucose or any other solute may be added to the solution, for example, in the amount sufficient to make the solution isotonic.

In addition to the dosage form for oral administration mentioned above, the therapeutic agent for renal failure of the present invention may be prepared in various dosage forms, such as various types of injections and suppositories for parenteral administration.

EXAMPLES

The present invention will be described more in detail with reference to the following examples.

Example 1

Effect of Beraprost Sodium on 5/6 Nephrectomized Rat Model

The effect of beraprost sodium on a 5/6 nephrectomized rat model, which has been widely used as a model animal for renal failure, was examined. Two-thirds of the left kidney was removed from each of 4-week-old male Wistar rats (Charles River Japan Inc.) with a razor, and all of the right kidney was then removed therefrom one week after. Three weeks after the initial surgery, blood was collected from each rat through the tail vein and serum creatinine and BUN levels were determined from the blood. At this point of time, the urine was also collected for 24 hours to determine the mass of proteins in the urine. The rats were allocated to one of the treatment groups by the stratifying continuous randomization method based on the mass of proteins in the urine and the body weight (n=8 per group). There was observed little difference in the initial values of blood creatinine and BUN values among the rats. Three weeks after the initial surgery, beraprost sodium or captopril (SIGMA, i.e., a positive control) was orally administered to each rat twice a day everyday, beginning the day on which administration of a drug was started and continued through five weeks after the administration. The determination of the renal functions was performed both three weeks and five weeks after the initial administration of a drug. The photographic images of the renal tissue were observed only five weeks after the initial administration. In the sham surgery group ("sham") in which no drug was administered, increased BUN level (which is a measure of the progress of chronic renal failure) was observed three weeks after the initial administration, which indicated that chronic renal failure was advanced. Five weeks after the initial administration, more exacerbation of chronic renal failure was observed. In the beraprost sodium-administered group, significant prevention of increase in the urinary protein level and prevention of reduction in the creatinine clearance and increase in the BUN level were observed three weeks after the initial administration (Table 1). The same tendency was shown five weeks after the initial administration (Table 2). As demonstrated by the observation of renal tissue images five weeks after the initial administration, the progress of the glomerular conditions was markedly prevented (Table 3). In the positive control group (i.e., the captopril-administered group), the similar ameliorative effects were shown. These results clearly demonstrate that beraprost sodium can improve the conditions of renal failure rats.

TABLE 1

Effect of beraprost on chronic renal failure model rats
(three weeks after the administration of a drug)

| Drug | Body weight (g) | Urinary volume (ml/24 hr) | Urinary protein excretion (mg/24 hr/kgBW) | Creatinine clearance (µl/min/100 gBW) | Blood urea nitrogen (µg/dl) |
|---|---|---|---|---|---|
| Sham | 229.4 ± 6.1 | 32.3 ± 3.7 | 3.6 ± 0.6 | 430.9 ± 15.3 | 14.9 ± 1.1 |
| Control | 224.8 ± 6.9 | 18.4 ± 1.7** | 320.6 ± 69.7** | 132.7 ± 19.9** | 58.9 ± 7.7** |
| Captopril (50 mg/kg) | 220.6 ± 5.4 | 21.7 ± 3.7 | 136.8 ± 29.9 | 151.9 ± 12.3 | 51.4 ± 3.7 |
| TRK-100 (100 µg/kg) | 215.5 ± 5.3 | 20.1 ± 2.8 | 125.3 ± 20.8# | 134.1 ± 11.0 | 55.9 ± 3.7 |
| TRK-100 (300 µg/kg) | 221.0 ± 6.3 | 20.4 ± 3.7 | 154.8 ± 53.0# | 136.4 ± 9.9 | 50.9 ± 3.6 |

Values represent mean ± s.e.m. from 8 rats.
**represents the control group having a significant difference from the sham group ($p < 0.01$).
($p < 0.05$) and
($p, 0.01$) represent the drug-administered groups having a significant difference from the control group.

TABLE 2

Effect of beraprost on chronic renal failure model rats
(five weeks after the administration of a drug)

| Drug | Body weight (g) | Urinary volume (ml/24 hr) | Urinary protein excretion (mg/24 hr/kgBW) | Creatinine clearance (µl/min/100 gBW) | Blood urea nitrogen (µg/dl) |
|---|---|---|---|---|---|
| Sham | 238.4 ± 7.1 | 24.7 ± 4.1 | 7.8 ± 0.7 | 365.6 ± 20.1 | 16.9 ± 1.1 |
| Control | 237.2 ± 8.1 | 22.1 ± 3.6 | 301.4 ± 51.6** | 135.4 ± 22.9** | 55.2 ± 9.7** |
| Captopril (50 mg/kg) | 236.4 ± 5.7 | 21.9 ± 3.2 | 255.5 ± 76.6 | 161.1 ± 17.3 | 47.8 ± 5.2 |

TABLE 2-continued

Effect of beraprost on chronic renal failure model rats
(five weeks after the administration of a drug)

| Drug | Body weight (g) | Urinary volume (ml/24 hr) | Urinary protein excretion (mg/24 hr/kgBW) | Creatinine clearance (µl/min/100 gBW) | Blood urea nitrogen (µg/dl) |
|---|---|---|---|---|---|
| TRK-100 (100 µg/kg) | 228.7 ± 5.7 | 21.7 ± 3.1 | 276.5 ± 69.2 | 156.9 ± 19.5 | 45.5 ± 3.3 |
| TRK-100 (300 µg/kg) | 245.8 ± 8.0 | 20.4 ± 1.7 | 197.1 ± 21.1 | 143.5 ± 10.0 | 45.1 ± 3.5 |

Values represent mean ± s.e.m. from 7-8 rats.
\*\*represents the control group having a significant difference from the sham group ($p < 0.01$).

TABLE 3

| Region | Histopathological change | Sham | Control | Captopril (50 µg/kg) | BPS (100 µg/kg) | BPS (300 µg/kg) |
|---|---|---|---|---|---|---|
| Renal corpuscle | Glomerular hypertrophy | 0 | 8 | 1 | 3 | 2 |
| | Cellular filling in glomerulus | 0 | 7 | 4 | 7 | 4 |
| | Glomerulosclerosis | 0 | 3 | 2 | 2 | 1 |
| | Epidermal growth in Bowman's capsule | 0 | 5 | 2 | 1 | 1 |
| | Deposition of PAS + materials in Bowman's capsule | 0 | 3 | 1 | 2 | 1 |
| | Coagulation of glomeruli in Bowman's capsule | 0 | 5 | 2 | 2 | 1 |
| Uriniferous tuble | Basophilic degeneration of tubules | 0 | 8 | 6 | 8 | 8 |
| | Proliferation of proximal tubules | 0 | 8 | 8 | 8 | 8 |
| | Tubular dilation | 0 | 8 | 8 | 8 | 8 |
| | Proteinaceous urinary casts | 0 | 8 | 4 | 5 | 2 |
| Framework | Infiltration of mononuclear cells | 0 | 6 | 7 | 1 | 7 |

Each value represents the number of animals in which histopathological change was observed in 8 animals per group.

Example 2

Renal failure rat models of which the primary disease was glomerulonephritis were used to examine the effect of different 4,8-inter-m-phenylene prostaglandin $I_2$ derivatives including beraprost sodium on the models. Eight-week-old male WKY rats (Charles River Japan Inc.) were administered intravenously with rabbit anti-rat glomerular basement membrane antiserum to induce glomerulonephritis. Two weeks after the induction, blood was collected from each rat through the tail vein to determine blood creatinine and BUN levels. The blood creatinine and BUN levels in the glomerulonephritis-induced rats were remarkably higher than those in the non-induced rats, which indicated that the conditions of the rats progressed into renal failure. Four types of 4,8-inter-m-phenylene prostaglandin $I_2$ derivatives in total, including beraprost sodium, were individually administered subcutaneously to the rats from the back continuously with an osmotic pump (ALZET) for one week, beginning two weeks after induction of glomerulonephritis and continued through three weeks after the induction. The renal functions (i.e., blood creatinine and BUN levels) were determined one week after the initial administration of a drug. In a glomerulonephritis-induced group to which no drug was administered (i.e., a control group), blood creatinine and the BUN levels determined three weeks after the induction of glomerulonephritis were increased compared with those determined two weeks after the induction, which indicated that the conditions of the rats progressed into chronic renal failure. In a beraprost sodium-administered group, blood creatinine and BUN levels determined three weeks after the induction of glomerulonephritis were significantly decreased compared with those in the control group (Table 4). In groups to which other three types of 4,8-inter-m-phenylene prostaglandin $I_2$ derivatives (i.e., compounds 1, 2 and 3 shown below) were respectively administered, the similar ameliorative effect was observed (Table 5).

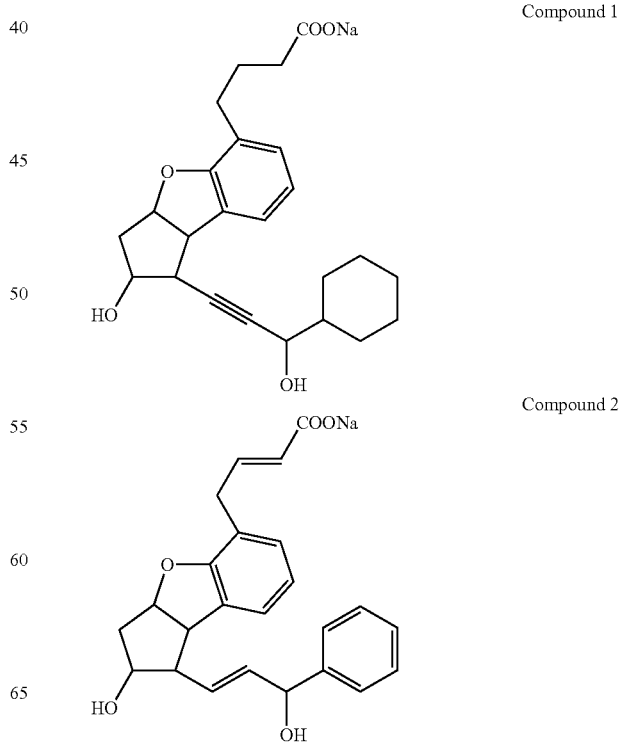

Compound 1

Compound 2

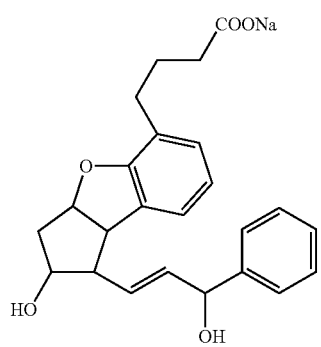

Compound 3

These results indicate that the 4,8-inter-m-phenylene prostaglandin I₂ derivatives including beraprost sodium can improve the conditions of rats with renal failure.

TABLE 4

Effect of beraprost sodium on renal failure rat models of which the primary disease is glomerulonephritis

| | Blood creatinine (mg/dl) | | BUN (mg/dl) | |
|---|---|---|---|---|
| | 2 weeks after induction (before administration) | 3 weeks after induction (1 week after the initial administration) | 2 weeks after induction (before administration) | 3 weeks after induction (1 week after the initial administration) |
| Normal group | 0.32 ± 0.02 | 0.30 ± 0.01 | 11 ± 1 | 18 ± 1 |
| Control group | 0.64 ± 0.09* | 0.89 ± 0.12* | 33 ± 7* | 40 ± 3* |
| Beraprost sodium-administered group | | | | |
| 60 µg/kg | 0.61 ± 0.07* | 0.48 ± 0.04# | 28 ± 3* | 31 ± 2# |
| 200 µg/kg | 0.62 ± 0.06* | 0.49 ± 0.04# | 30 ± 3* | 25 ± 1# |

*$p < 0.05$ vs. normal group (Student's t-test)
$p < 0.05$ vs. control group (Dunnett method)

TABLE 5

Effect of different 4,8-inter-m-phenylene prostaglandin I₂ derivatives on renal failure rat models of which the primary disease is glomerulonephritis

| | Blood creatinine (mg/dl) | | BUN (mg/dl) | |
|---|---|---|---|---|
| | 2 weeks after induction (before administration) | 3 weeks after induction (1 week after the initial administration) | 2 weeks after induction (before administration) | 3 weeks after induction (1 week after the initial administration) |
| Normal group | 0.30 ± 0.02 | 0.29 ± 0.02 | 19 ± 1 | 19 ± 1 |
| Control group | 0.44 ± 0.03* | 0.65 ± 0.04* | 23 ± 2* | 44 ± 2* |
| 4,8-inter-m-phenylene prostaglandin I₂ derivative-administered group | | | | |
| Compound 1 60 µg/kg | 0.44 ± 0.05* | 0.41 ± 0.02# | 29 ± 2* | 27 ± 2# |
| Compound 2 60 µg/kg | 0.45 ± 0.04* | 0.44 ± 0.05# | 28 ± 2* | 31 ± 3# |
| Compound 3 60 µg/kg | 0.45 ± 0.05* | 0.39 ± 0.04# | 28 ± 3* | 30 ± 3# |

*$p < 0.05$ vs. normal group (Student's t-test)
$p < 0.05$ vs. control group (Dunnett method)

Example 3

Glomerulonephritis rat models were used to examine the effect of beraprost sodium on the rat models both in a stage where renal failure had not been found (i.e., the inflammatory stage) and a stage where BUN level was increased and the conditions were progressed into renal failure (i.e., the renal failure stage). Eight-week-old male WKY rats (Charles River Japan Inc.) were administered intravenously with rabbit anti-rat glomerular basement membrane antiserum to induce glomerulonephritis. Each of beraprost sodium, captopril (SIGMA) and prednisolone (Shionogi & Co., Ltd.) was orally administered to the rats everyday either for one week from day 1 through day 7 after induction of glomerulonephritis (i.e., during the inflammatory stage) or for two weeks beginning two weeks after the induction through four weeks after the induction (i.e., during the renal failure stage). The frequency of the administration was twice a day for beraprost sodium and captopril and once a day for prednisolone. After the initial administration of a drug, urinary total protein excretion (which is a measure of renal functions) was determined. In the inflammatory stage (i.e., from day 1 through day 7 after induction of glomerulonephritis), the urinary total protein excretion in a glomerulonephritis-induced group to which no drug was administered (i.e., a control group) was remarkably increased compared with that in a non-glomerulonephritis-induced group (i.e., a normal group) (Table 6). In a beraprost sodium-administered group, the increase in urinal total protein excretion was markedly prevented (Table 6). In both captopril- and prednisolone-administered groups, effective prevention of increase in urinal total protein excretion was observed (Table 6). On the other hand, in the renal failure stage (i.e., from two weeks after induction of glomerulonephritis through four weeks after the induction), the urinary total protein excretion in the glomerulonephritis-induced group without administration of a drug (i.e., the control group) was remarkably increased compared with that in a non-glomerulonephritis-induced group (i.e., a normal group); in contrast, in the beraprost sodium-administered group, the increase in urinal total protein excretion was markedly prevented (Table 6). In both the captopril- and prednisolone-administered groups, no effective prevention of increase in urinal total protein excretion was observed (Table 6).

These results indicate that both prednisolone and captopril are not effective on the rats in the renal failure stage although they are effective on the rats in the inflammatory stage. In contrast, it is clearly indicated that beraprost sodium can improve the conditions of the rats both in the inflammatory stage and the renal failure stage.

TABLE 6

Effect of beraprost sodium, captopril and prednisolone on glomerulonephritis model rats in inflammatory and renal failure stages

| | Urinary total protein excretion (mg/24 hr) | | | | |
|---|---|---|---|---|---|
| | Inflammatory stage | Renal failure stage | | | |
| | | Exp. 1 | | Exp. 2 | |
| | 7 days after induction (1 week after initial administration) | 2 weeks after induction (before administration) | 3 weeks after induction (1 week after initial administration) | 2 weeks after induction (before administration) | 4 weeks after induction (2 week after initial administration) |
| Normal group | 19 ± 1 | 30 ± 6 | 20 ± 2 | 14 ± 1 | 17 ± 1 |
| Control group | 138 ± 9* | 370 ± 30* | 423 ± 55* | 324 ± 18* | 451 ± 77* |
| Beraprost-administered group | | | | | |
| 300 µg/kg | 17 ± 7# | 374 ± 21* | 300 ± 51# | 321 ± 23* | 295 ± 46# |
| Captopril-administered group | | | | | |
| 50 mg/kg | 75 ± 14# | N.D. | N.D. | 318 ± 22* | 504 ± 51 |
| 100 mg/kg | N.D. | N.D. | N.D. | 325 ± 6* | 517 ± 33 |
| Prednisolone-administered group | | | | | |
| 2 mg/kg | 38 ± 8# | 368 ± 20 | 456 ± 78 | N.D. | N.D. |

*p < 0.05 vs. normal group (Student's t-test)
p < 0.05 vs. control group (Dunnett method)
N.D.: Not determined.

INDUSTRIAL APPLICABILITY

The present invention provides a therapeutic agent for renal failure comprising, as an active ingredient, a 4,8-inter-m-phenylene prostaglandin $I_2$ derivative.

The invention claimed is:

1. A method for treatment of chronic renal failure comprising orally administering a therapeutically effective amount of a 4,8-inter-m-phenylene prostaglandin $I_2$ derivative represented by the following formula (I) or a pharmacologically acceptable salt thereof:

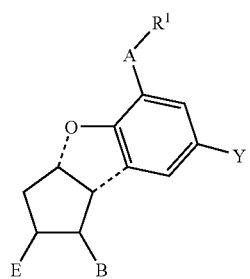

(I)

wherein:
R$^1$ represents COOR$^2$ wherein R$^2$ represents hydrogen or a pharmacologically acceptable positive ion;
A represents:
1) —(CH$_2$)$_m$—; or
2) —CH$_2$—CH═CH—
wherein in represents 3;

Y represents hydrogen;

B represents —X—C(R$^{11}$)(R$^{12}$)OR$^{13}$ wherein each of R$^{11}$ and R$^{13}$ represents hydrogen;

X represents:
1) —CH═CH—; or
2) —C≡C—; and
R$^{12}$ represents:
1) —Z—Ar$^2$;
2) —Z—R$^3$; or
3) —C$_u$H$_{2u}$—C≡C—R$^{17}$
wherein Z represents a valence bond; Ar$^2$ represents phenyl; R$^3$ represents cyclohexyl; u represents 3; C$_u$H$_{2u}$ represents a branched alkylene group; and R$^{17}$ represents methyl;
E represents —OH; and the formula (I) represents a d-form, l-form or dl-form,
to a patient with chronic renal failure, wherein said chronic renal failure in said patient has advanced and is characterized by:
a) Blood urea nitrogen (BUN) of 60 mg/dl or higher,
b) Congestive heart failure or lung congestion associated with reduced urinary volume,
c) Neurological or mental complaints associated with advanced uremia,
d) Hyponatremia or hyperkalemia,
e) Anemia caused by reduced production of erythropoietin in the kidney, or
f) Uremic symptoms caused by the advanced disorders or renal function.

2. The method for treatment of chronic renal failure according to claim 1, wherein the 4,8-inter-m-phenylene prostaglandin $I_2$ derivative is represented by the following formula (I):

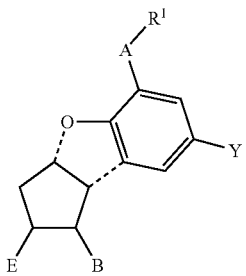

wherein:
  $R^1$ represents $COOR^2$ wherein $R^2$ represents hydrogen or a pharmacologically acceptable positive ion;
  A represents —$(CH_2)_m$—
    wherein m represents 3;
  Y represents hydrogen;
  B represents —X—$C(R^{11})(R^{12})OR^{13}$
    wherein each of $R^{11}$ and $R^{13}$ represents hydrogen;
  X represents —CH=CH—; and
  $R^{12}$ represents —$C_uH_{2u}$—C≡C—$R^{17}$
    wherein u represents 3; $C_uH_{2u}$ represents a branched alkylene group; and $R^{17}$ represents methyl;
  E represents —OH; and the formula (I) represents a d-form, l-form or dl-form.

3. The method according to claim 1, wherein the 4,8-inter-m-phenylene prostaglandin $I_2$ derivative is beraprost or a salt thereof.

4. The method according to claim 1, wherein a causal disease of the chronic renal failure is glomerulonephritis, nephrosclerosis or diabetic nephropathy.

5. The method according to claim 1, wherein said chronic renal failure is defined by an increase in serum creatinine level and/or blood urea nitrogen level.

6. The method according to claim 1, wherein said chronic renal failure is progressive chronic renal failure in which serum creatinine level and/or blood urea nitrogen level increase(s) with time.

7. The method according to claim 1, wherein increase in serum creatinine level and/or blood urea nitrogen level is(are) reduced, or the serum creatinine level and/or blood urea nitrogen level is(are) decreased.

8. A method for treatment of chronic renal failure comprising orally administering a therapeutically effective amount of a 4,8-inter-m-phenylene prostaglandin $I_2$ derivative represented by the following formula (I) or a pharmacologically acceptable salt thereof:

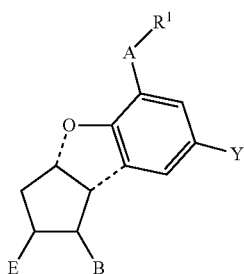

wherein:
  $R^1$ represents $COOR^2$ wherein $R^2$ represents hydrogen or a pharmacologically acceptable positive ion;
  A represents:
    1) —$(CH_2)_m$—; or
    2) —$CH_2$—CH=CH—
      wherein m represents 3;
  Y represents hydrogen;
  B represents —X—$C(R^{11})(R^{12})OR^{13}$
    wherein each of $R^{11}$ and $R^{13}$ represents hydrogen;
  X represents:
    1) —CH=CH—; or
    2) —C≡C—; and
  $R^{12}$ represents:
    1) —Z—$Ar^2$;
    2) —Z—$R^3$; or
    3) —$C_uH_{2u}$—C≡C—$R^{17}$
      wherein Z represents a valence bond; $Ar^2$ represents phenyl; $R^3$ represents cyclohexyl; u represents 3; $C_uH_{2u}$ represents a branched alkylene group; and $R^{17}$ represents methyl;
  E represents —OH; and the formula (I) represents a d-form, l-form or dl-form,
to a patient with chronic renal failure, wherein the patient is undergoing dialysis treatment.

9. A method for treatment of chronic renal failure comprising orally administering a therapeutically effective amount of a 4,8-inter-m-phenylene prostaglandin $I_2$ derivative represented by the following formula (I) or a pharmacologically acceptable salt thereof:

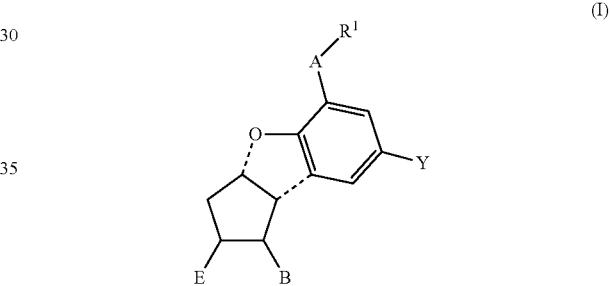

wherein:
  $R^1$ represents $COOR^2$ wherein $R^2$ represents hydrogen or a pharmacologically acceptable positive ion;
  A represents:
    1) —$(CH_2)_m$—; or
    2) —$CH_2$—CH=CH—
      wherein m represents 3;
  Y represents hydrogen;
  B represents —X—$C(R^{11})(R^{12})OR^{13}$
    wherein each of $R^{11}$ and $R^{13}$ represents hydrogen;
  X represents:
    1) —CH=CH—; or
    2) —C≡C—; and
  $R^{12}$ represents:
    1) —Z—$Ar^2$;
    2) —Z—$R^3$; or
    3) —$C_uH_{2u}$—C≡C—$R^{17}$
      wherein Z represents a valence bond; $Ar^2$ represents phenyl; $R^3$ represents cyclohexyl; u represents 3; $C_uH_{2u}$ represents a branched alkylene group; and $R^{17}$ represents methyl;
  E represents —OH; and the formula (I) represents a d-form, l-form or dl-form, to a patient with chronic renal failure, wherein dialysis has been recommended for said patient.

* * * * *